United States Patent

Munro et al.

Patent Number: 5,262,388
Date of Patent: Nov. 16, 1993

[54] HERBICIDAL COMPOUNDS

[75] Inventors: David Munro, Maidstone; Bipin Patel, Sittingbourne, both of England

[73] Assignee: Shell Research Limited, United Kingdom

[21] Appl. No.: 871,062

[22] Filed: Apr. 20, 1992

[30] Foreign Application Priority Data

May 20, 1991 [GB] United Kingdom ............... 9110858

[51] Int. Cl.[5] .............. A01N 43/74; C07D 261/04
[52] U.S. Cl. ............................ 504/271; 548/240
[58] Field of Search .............. 548/240; 71/88; 504/271

[56] References Cited

U.S. PATENT DOCUMENTS 4,261,728  4/1981  Franz et al. ..................... 71/88

FOREIGN PATENT DOCUMENTS 0174685  3/1986  European Pat. Off. ........... 548/240
0187345  7/1986  European Pat. Off. ........... 548/240
0334120  9/1989  European Pat. Off. ........... 548/240

OTHER PUBLICATIONS

CA 112:178948j Isoxazolines . . . herbicides. Rheinheimer et al., p. 766, 1990.
CA 115:8637b Synthesis . . . alcohols. Kanemasa et al., p. 844, 1991.
Houk et al., *J. Amer. Chem. Soc.*, 1984, vol. 106, pp. 3880–3882.

Primary Examiner—Mary C. Lee
Assistant Examiner—Joseph K. McKane

[57] ABSTRACT

Compounds of formula

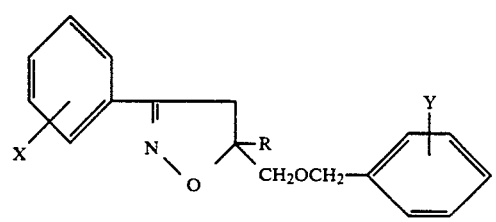

(I)

in which
X is nitro;
Y is hydrogen or halogen; and
R is $C_{1-6}$ alkyl;
are useful as herbicides, especially against grass weeds of rice crops.

10 Claims, No Drawings

HERBICIDAL COMPOUNDS

The present invention is concerned with certain isoxazoline compounds, their preparation and their use as herbicides.

Barnyard grass is an important annual weed of, inter alia, rice crops. There is a need for a selective herbicide that can control barnyard grass yet not cause damage to crop plants. Desirably, with ever-increasing concern over the amount of residue that can arise from the release of chemicals into the environment, such selective control should be achieved at low dose rate applications. Rice can be grown either by transplantation into paddy fields or by direct-seeding onto the crop site. Barnyard grass, the Echinochloa species, is an important weed of both types of rice crop. A particularly important weed of paddy field rice crops is the barnyard grass species, *Echinochloa oryzicola*.

European Patent Specification No. 334 120 A1 discloses, as herbicides, a broad class of isoxazoline compounds of which 128 compounds are specifically identified. Compounds of the class were tested in glasshouse trials at application rates of 0.5 and 1.0 kg/ha of active ingredient. The results highlight the particular usefulness of certain compounds in combating weeds in the crops of oil-seed rape and sunflower and in combating *Chenopodium album*, a weed species which commonly affects North European cereals, maize, potato, sugar beet and sunflower crops. The list of test plants used in the glasshouse trials includes *Echinochloa crus-galli*, a common variety of barnyard grass, but no significant herbicidal action against that species has been noted.

It has now been found that a certain small group of isoxazolines which is outside the class of isoxazolines of EP-A-334 120 has especially useful herbicidal properties. In particular the novel compounds exhibit a markedly high herbicidal activity against important Echinochloa species at low dose rate levels which is greater than that shown by structurally similar compounds specifically disclosed in EP-A-334 120, whilst showing no detrimental effect on rice plants, whether direct-seeded or transplanted.

The present invention provides a compound of the general formula

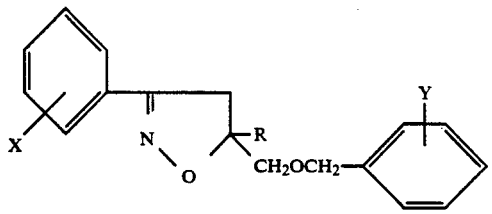

in which
X represents a nitro group;
Y represents a hydrogen or halogen atom; and
R represents a $C_{1-6}$ alkyl group.

The nitro group, X, may be at any position on the 3-phenyl group. Preferably, however, the group X is positioned ortho to the isoxazole ring linkage.

The other aromatic ring in the compounds of the present invention may be unsubstituted, i.e. Y is hydrogen, or substituted by a halogen atom. Suitably the halogen is fluorine, chlorine, bromine or iodine. Preferably the halogen substituent is fluorine. The substitution may occur at any position on the phenyl ring, but it is preferred for the halogen substitution to be ortho to the methylene group, i.e. preferably that Y is 2-fluoro.

The group R at the 5-position on the isoxazoline ring may be a straight chain or branched chain $C_{1-6}$ alkyl group. Preferably R is a $C_{1-3}$ alkyl group, especially a methyl group.

The present invention also provides a process for the preparation of a compound of the general formula I, which comprises reacting a benzyl allyl ether of the general formula

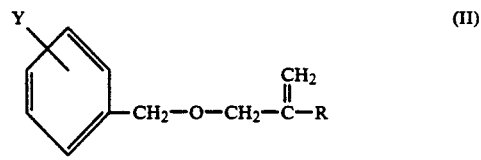

in which Y and R are as hereinbefore defined, With an oxime of the general formula

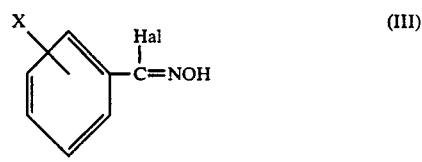

in which X is as hereinbefore defined and Hal represents a halogen atom, preferably chlorine or bromine, in the presence of an acid scavenger and of an organic solvent.

The oxime of formula III yields a hydrogen halide during the reaction and generates a reactive, and unstable, intermediate nitrile oxide in situ which reacts immediately with the benzyl allyl ether of formula II to form the desired isoxazoline. The acid scavenger eliminates the hydrogen halide formed. Conveniently the acid scavenger and the solvent are selected such that the acid scavenger/halide by-product is insoluble in the solvent thus ensuring easy separation.

The acid scavenger is suitably a tertiary amine, for example a trialkylamine of up to four carbon atoms. The solvent is conveniently a dialkyl ether of up to four carbon atoms. Especially suitable is the use of triethylamine as the acid scavenger and diethyl ether as the solvent. Preferably an excess of the acid scavenger is used, for example up to 50%, usefully a 20% excess.

The regiochemistry of this addition reaction is well known in the art, see, for example, page 98 of the book "The Nitrile Oxides" by C. H. Grundmann and P. Grinager, published by Springer Verlag in 1971.

The process of the present invention is typically carried out at below ambient temperature, for example suitably from $-10°$ C. to $10°$ C., and conveniently at $0°$ C. Suitably the reactants are employed in a substantially 1:1 molar ratio.

Preferably the reaction is carried out using dried materials and under anhydrous conditions.

Following separation of the acid scavenger/hydrogen halide by-product, the isoxazolines of the present invention may be isolated and purified by conventional techniques, for example by chromatographic techniques. Generally the isoxazolines are oils which are unstable to distillation, even under reduced pressure which therefore cannot be used as a means of purification. However, over time the oils may solidify and further purification by recrystallisation may then be possible, if desired.

The oxime of formula III is suitably itself freshly prepared for use in the reaction of the invention. The desired instability which gives rise to the elimination of hydrogen halide and the formation of the transient nitrile oxide intermediates, also, unfortunately, is such that in the absence of another reactant, the oxides formed will react with themselves to give unwanted furoxan products.

The compounds of formula III are suitably prepared from a corresponding nitrobenzaldoxime by conventional halogenation techniques. A suitable halogenation agent is N-chlorosuccinimide or N-bromosuccinimide. The halogenation is usefully carried out in an organic solvent, for example a dialkylformamide of up to 4 carbon atoms, conveniently dimethylformamide, at elevated temperature, for example at a temperature in the range of from 20° to 70° C., suitably 50° C. Care has to be taken in the addition of the halogenation agent to the reaction medium, and it is useful to stagger the addition of the agent in the early stages of the reaction.

It is convenient to purify the compound of formula III prepared by such a method, by solvent extraction using, for example, water and an organic solvent which is the same as that required for the process of the invention. The reactant can then be used directly to minimise loss by decomposition to the unwanted furoxans. Thus, usefully, solvent extraction is performed using water and diethyl ether, followed by drying of the separated organic layer to maintain the preferred dry conditions for the preparation of the isoxazolines.

The starting nitrobenzaldoximes are known or preparable by conventional techniques from the corresponding nitrobenzaldehydes, which are well documented compounds (see, for example The Merck Index, 11, 6508).

The benzyl allyl ethers of formula II may be prepared by reacting a 2-($C_{1-6}$ alkyl)propen-1-ol or a salt thereof, in which the alkyl group, which corresponds to the 'R' in formula I, is especially a methyl group, with an optionally halo-substituted benzyl halide. The halide is suitably a chloride or a bromide, preferably a bromide. The reaction is suitably carried out in a non-protic solvent. Suitably the propanol is employed in the form of a salt, usefully an alkali metal salt, conveniently the sodium salt, which may be prepared by conventional techniques, for example by reaction of the propanol with an alkali metal hydride in an organic solvent.

The starting alkyl propen-1-ols and the required benzyl halides are well known or easily preparable by standard methods. Benzyl bromide, for example, features in The Merck Index, 11, 1142, and 2-methylpropen-1-ol in Beilstein, 1, 443.

The compounds of the present invention have interesting herbicidal properties, both pre-emergence and post-emergence, and have been found to be extremely effective in particular against the important grass weed Echinochloa, which effect is maintained at low dosage rates. Furthermore the compounds have an associated rice tolerance, giving no adverse effect against pre-seeded or transplanted rice species at low or high dose rates.

Thus the compounds of the present invention find especial use in the control of undesired plant species, e.g. grass weeds such as *Echinochloa crus-galli* and especially *Echinochloa oryzicola* in rice crops.

Accordingly, the invention further provides a herbicidal composition comprising a compound of formula I as defined above in association with a carrier, and a method of making such a composition which comprises bringing a compound of formula I into association with a carrier.

The invention also provides the use of such a compound or composition according to the invention as a herbicide. Further, in accordance with the invention, there is provided a method of combating undesired plant growth at a locus by treating the locus with a compound or composition according to the invention. Application to the locus may be pre-emergence or post-emergence. The dosage of active ingredient used, may, for example, be in the range of from 0.01 to 10 kg/ha, suitably 0.05 to 1 kg/ha. The locus may, for example, be the soil or plants in a crop area, typical crops being rice crops such as *Oryza sativa*, whether direct-seeded or transplanted.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other active ingredients, for example compounds possessing insecticidal or fungicidal properties, or other herbicides.

The following Examples illustrate the inventio The structures of the compounds of general formula I prepared in the Examples were confirmed by mass spectrometry and NMR.

EXAMPLE 1

3-(2-nitrophenyl)-5-methyl-5-(2-fluorobenzyloxymethyl) isoxazoline (a) Oil-free sodium hydride (4 g) was added to dry tetrahydrofuran (100 mls) and 2-methyl-2-propen-1-ol (12 g) in dry tetrahydrofuran (50 ml) was added dropwise with stirring under nitrogen. When evolution of hydrogen had ceased, 2-fluorobenzylbromide (31.5 g) was added and the reaction mixture refluxed with stirring for 1 hour.

Most of the tetrahydrofuran was then removed in vacuo, and the residue partitioned between chloroform (500 ml) and water (500 ml). The organic layer was separated, washed and dried and the solvent removed to give a yellow oil. This was chromatographed on a silica column using a mixture of chloroform and hexane [50%/50%] as eluent, to give a colourless oil (23.4 g; yield 78%). This material was used in step (c) below.

(b) 2-Nitrobenzaldoxime (16.6 g) was dissolved in dimethylformamide (100 mls). N-chlorosuccinimide (1.5 g) was added to the solution with stirring and the reaction mixture heated to 45° to 50° C. to initiate the reaction. A further 11.9 g of N-chlorosuccinimide was added in approximately 1 g amounts over the course of 1 hour. Alternate heating or cooling was often necessary to maintain the temperature in the desired range. The reaction mixture was then allowed to cool before pouring into water (400 mls) and extracting into diethyl ether (2×250 mls). The organic layer was separated and dried over sodium sulphate. After filtering off the drying agent, the ether solution was used directly in step (c) below.

(c) 2-Fluorobenzyl allyl ether of step (a) [16.2 g; 0.09 mole] was added to the ether solution of step (b), cooled to 0° C., and triethylamine (11 g; 20% excess) added dropwise with stirring, over the course of 1 hour.

The precipitate of triethylamine hydrochloride was filtered off and the solvent removed from the filtrate in vacuo to give a yellow oil. This was chromatographed [silica; CHCl$_3$] to give a pale yellow oil (12.7 g; yield 41%). The spectral properties of the material were in accord with its assigned structure.

EXAMPLEs 2 TO 4

Following the procedure of Example 1 above, further compounds of the invention were prepared. The details of the compounds are given in Table 1 below in which the compounds are identified by reference to the substituents of formula I.

TABLE 1

| Example No. | R | X | Y |
|---|---|---|---|
| 2 | CH$_3$ | 2-NO$_2$ | H |
| 3 | CH$_3$ | 3-NO$_2$ | H |
| 4 | CH$_3$ | 4-NO$_2$ | H |

The physical property data for the compounds of Examples 1 to 4 are given in Table 2 below.

TABLE 2

| Example No. | Melting Point (°C.) | Elemental Analysis (Calc/Found) C | H | N | or | $^1$H NMR Shift (δ) | Multiplicity | Coupling (Hz) | |
|---|---|---|---|---|---|---|---|---|---|
| 1 | Oil | | | | | 7.95–7.2 | m | | 8H aromatic |
| | | | | | | 4.63 | d of d | J = 3.5/2.5 | 2H ether |
| | | | | | | 3.6 | d of d | J = 5/2 | 2H ether |
| | | | | | | 3.15 | d of d | J = 22/3.5 | 2H isoxazoline |
| | | | | | | 1.52 | s | | 3H methyl |
| 2 | 62 | 66.3 | 5.5 | 8.6 | | | | | |
| | | 66.6 | 5.7 | 8.6 | | | | | |
| 3 | Oil | | | | | 8.35–7.2 | m | | 9H aromatic |
| | | | | | | 4.6 | d of d | J = 4/2 | 2H ether |
| | | | | | | 3.56 | d of d | J = 5/2 | 2H ether |
| | | | | | | 3.25 | d of d | J = 27/3.5 | 2H isoxazoline |
| | | | | | | 1.48 | s | | 3H methyl |
| 4 | Oil | | | | | 8.0 | d of d | J = 26/2 | 4H aromatic AA'BB' |
| | | | | | | 7.35–7.2 | m | | 5H aromatic |
| | | | | | | 4.62 | d of d | J = 4/2 | 2H ether |
| | | | | | | 3.58 | d of d | J = 5/2 | 2H ether |
| | | | | | | 3.25 | d of d | J = 28/3.5 | 2H isoxazoline |
| | | | | | | 1.5 | s | | 3H methyl |

EXAMPLE 5

Herbicidal Activity

To evaluate their herbicidal activity, compounds according to the invention and structurally similar compounds specifically disclosed in EP-A-334 120, were tested using as a representative range of plants: maize, Zea mays (Mz); rice, Oryza sativa (R); barnyard grass, Echinochloa crus-galli (BG); oat, Avena sativa (O); linseed, Linum usitatissimum (L); mustard, Sinapsis alba (M); sugar beet, Beta vulgaris (SB) and soya bean, Glycine max (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in the following Table 3 in which the compounds of the present invention are identified by reference to the preceding Examples. A blank space in the Table indicates a 0 rating. The compounds of EP-A-334 120 tested are designated in the following Table as Compounds A and B. Compound A is specifically disclosed in EP-A-334 120 as Compound No. 49 and Compound B is specifically disclosed in the document as Compound No. 118.

From the results it can be seen that the compounds of the present invention have a consistently high herbicidal effect against Echinochloa crus-galli in both pre- and post- emergence tests, which effect is maintained at the lower dose rates tested.

TABLE 3

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| A | 4 | 2 | 6 | 4 | 2 | | 4 | | 5 | 4 | 1 | 8 | | 6 | 4 | 6 | 4 | 2 | | 8 | | | | 5 | |
| | | | | | | | | | 1 | 1 | | 6 | | 4 | 2 | 3 | 1 | 1 | | 8 | | | | 4 | |
| B | 2 | | 7 | 3 | 3 | 2 | | 2 | 5 | 2 | | 7 | 2 | 5 | 5 | 3 | 2 | | | 5 | 3 | | | | |
| | | | | | | | | | 1 | | | 2 | | 2 | 2 | | | | | 3 | 2 | | | | |
| 1 | 8 | 4 | 8 | 7 | 3 | 3 | 4 | | 5 | 7 | | 8 | 2 | 7 | 4 | 4 | 4 | 3 | 5 | 9 | 2 | 4 | 2 | | |
| | | | | | | | | | 1 | 5 | | 8 | 1 | 6 | 3 | 3 | 2 | 1 | 2 | 8 | 1 | 3 | 1 | | |
| 2 | 7 | 6 | 9 | 5 | 3 | 3 | 5 | | 5 | 4 | | 8 | 1 | 7 | 5 | 5 | 2 | 3 | 3 | 8 | 2 | 2 | 2 | | |
| | | | | | | | | | 1 | 2 | | 7 | | 7 | 4 | 4 | 1 | 1 | 2 | 5 | | | | | |
| 3 | 3 | 3 | 8 | 6 | | | 2 | | 5 | 4 | | 8 | | 5 | 4 | 4 | 3 | | | 8 | | | | | |

TABLE 3-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 4 | | | 8 | | | | | | 1 | 1 | | 8 | 4 | 3 | 2 | 2 | | 7 | | | | | | | |
| | | | | | | | | | 5 | 2 | | 8 | 6 | 4 | 5 | 3 | | 5 | | | | | | | |
| | | | | | | | | | 1 | | | 7 | 4 | 3 | 2 | 2 | | 2 | | | | | | | |

EXAMPLE 6

Herbicidal Selectivity (a) The selectivity of action against barnyard grass species and rice plant species of the compound of Example 1 of the present application and Compounds A and B (Compounds Nos. 49 and 118 of EP-A-334 120) was investigated. Plants of the barnyard grass species Echinochloa crus-galli and Echinochloa oryzicola and plants of the rice species Oryza sativa were used in this test procedure. The barnyard grass species Echinochloa crus-galli (BGP) and Echinochloa oryzicola (BGO) were tested as direct-seeded plants. Plants of the rice species Oryza sativa were tested as direct-seeded plants (RIP) and also as transplanted plants (RIT).

For direct-seeded plants, seeds were sown in 12.5 cm deep pots containing a sterilised horticultural loam; when the shoots had just emerged the pots were flooded with water the level of which was maintained at 10 to 20 mm above the soil surface to simulate paddy field conditions. For transplanted plants, seedling plants were raised in minipots containing a sterilised horticultural loam and at an appropriate growth stage the plants and soil were transferred into a 12.5 cm pot, containing a sterilised horticultural loam, which was flooded with water to a level maintained at 10–20 mm above the soil surface.

The compounds were dissolved in a minimum amount of acetone, diluted with water and 5 ml applied evenly to the water in each 12.5 cm paddy pot. The dosage levels in these tests corresponded to application at 0.4, 0.1 and 0.025 kg/ha.

For each plant species two replicates were used for all treatments. Phytotoxicity was assessed visually after 11 days using a 0-100 scale. A rating 0 indicates growth as an untreated control; a rating 100 indicates death. The results are set out in the following Table 4.

TABLE 4

| Compound | Dosage (kg/ha) | Plant Species | | | |
|---|---|---|---|---|---|
| | | BGP | BGO | RIP | RIT |
| Ex. 1 | 0.4 | 97.00 | 87.50 | 0.00 | 0.00 |
| | 0.1 | 94.00 | 85.00 | 0.00 | 0.00 |
| | 0.025 | 27.50 | 7.50 | 0.00 | 0.00 |
| A | 0.4 | 95.50 | 65.00 | 0.00 | 0.00 |
| | 0.1 | 2.50 | 2.50 | 0.00 | 0.00 |
| | 0.025 | 0.00 | 0.00 | 0.00 | 0.00 |
| B | 0.4 | 86.50 | 17.50 | 0.00 | 0.00 |
| | 0.1 | 2.50 | 2.50 | 0.00 | 0.00 |
| | 0.025 | 0.00 | 0.00 | 0.00 | 0.00 |

As can be seen from the results, in simulated paddy field conditions none of the compounds adversely affects the growth of rice plants whether direct-seeded or transplanted, but the compound of the present invention has a significantly high herbicidal action against both Echinochloa species tested, which is maintained at the low dose rate of 0.1 kg/ha. The prior art compounds, although active against Echinochloa species at the higher dose rate, are inactive at the lower dose rates tested.

(b) The selectivity of action against Echinochloa oryzicola and rice plant species of the compound of Example 2 of the present application and of Compound No. 53 of EP-A-334 120 (hereinafter referred to as Compound C), was evaluated. The test procedure used was the same as that for Example 6a) except that the dosage levels for this test corresponded to application at 2.0, 0.6 and 0.2 kg/ha. The assessment of phytotoxicity was carried out at the same control plant growth stage as for Example 6a) above, and was taken after 14 days.

The results are set out in the following Table 5. Again the compound of the invention shows the higher activity against baryard grass species, which for Echinochloa Oryzicola is especially pronounced at the low test dose rate of 0.2 kg/ha.

TABLE 5

| Compound | Dosage (kg/ha) | Plant Species | | | |
|---|---|---|---|---|---|
| | | BGP | BGO | RIP | RIT |
| Ex. 2 | 2.0 | 100.00 | 92.50 | 0.00 | 0.00 |
| | 0.6 | 99.00 | 90.00 | 0.00 | 0.00 |
| | 0.2 | 98.00 | 85.00 | 0.00 | 0.00 |
| C | 2.0 | 100.00 | 95.00 | 0.00 | 0.00 |
| | 0.6 | 98.50 | 82.50 | 0.00 | 0.00 |
| | 0.2 | 91.50 | 0.00 | 0.00 | 0.00 |

(c) A statistical evaluation was carried out to enable a direct comparison of the activities of the compounds involved in each test. The phytotoxicity results of a) and b) above were subjected to a standard probit analysis by computer to calculate the dosage of each compound in kg/ha required to kill 50% and to kill 90% of the barnyard grass species. These dosages are termed the $GID_{50}$ and $GID_{90}$ respectively. Naturally the lower the amount the more effective the compound is against the weed species. The results of the statistical evaluation are given below in Tables 6a and 6b.

TABLE 6a

| Compound | $GID_{50}$ | |
|---|---|---|
| | BGP | BGO |
| A | 0.207 | 0.361 |
| B | 0.240 | 1.096 |
| C | 0.07 | 0.42 |
| Ex. 1 | 0.037 | 0.064 |
| Ex. 2 | 0.04 | 0.09 |

TABLE 6b

| Compound | $GID_{90}$ | |
|---|---|---|
| | BGP | BGO |
| A | 0.431 | 1.491 |
| B | 0.499 | 4.524 |
| C | 0.19 | 2.13 |
| 1 | 0.077 | 0.264 |
| 2 | 0.11 | 0.44 |

From the results, it can be seen that of the two 2-fluorobenzyloxymethyl compounds, that of Example 1 and Compound C, the compound of Example 1 has significantly lower $GID_{50}$ and $GID_{90}$ values showing it to be the most effective of the two compounds. The compounds of Examples 1 and 2, both 3-(2-nitrophenyl) isoxazoline compounds, show advantageously low $GID_{50}$ and $GID_{90}$ values compared with the 3-(unsubstituted phenyl) Compound A and the 3-(ortho-substituted phenyl) Compound B. Indeed, in each case the activity of the compounds of the present invention is shown to be significantly greater than that of the prior art Compounds A, B and C, and is particularly pronounced in respect of the important paddy rice weed species, *Echinochloa oryzicola*.

We claim:

1. A compound of the general formula

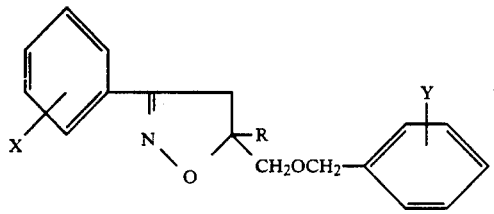

(I)

in which

X represents a nitro group;

Y represents a hydrogen or halogen atom; and

R represents a $C_{1-6}$ alkyl group.

2. A compound as claimed in claim 1, wherein the nitro group X is ortho to the linkage to the isoxazole ring.

3. A compound as claimed in claim 1, wherein Y represents a hydrogen or a fluorine atom.

4. A compound as claimed in claim 3, wherein Y is 2-fluoro.

5. A compound as claimed in claim 1, wherein R represents a methyl group.

6. A herbicial composition which comprises a compound as claimed in claim 1, together with a carrier.

7. A method of combating undesired plant growth at a locus which comprises treating the locus with a herbicidally effective amount of a compound as claimed in claim 1.

8. A method as claimed in claim 7, wherein the locus is a rice crop area.

9. A method of combating undesired plant growth at a locus which comprises treating the locus with a herbicidally effective amount of a composition as claimed in claim 6.

10. A method as claimed in claim 9, wherein the locus is a rice crop area.

* * * * *